United States Patent
Müller et al.

(10) Patent No.: US 6,248,338 B1
(45) Date of Patent: Jun. 19, 2001

(54) STARCHY CLEANING AND COSMETIC CARE PREPARATIONS

(75) Inventors: Wilfried Müller, Ubach-Palenberg; Rainer Vathie, Stolberg, both of (DE); Martin Scott Cardinali, Martinsville, NJ (US)

(73) Assignee: National Starch and Chemical Investment Holding Corporation, Wilmington, DE (US)

( * ) Notice: Subject to any disclaimer, the term of this patent is extended or adjusted under 35 U.S.C. 154(b) by 0 days.

(21) Appl. No.: 09/214,571

(22) PCT Filed: Jul. 7, 1997

(86) PCT No.: PCT/EP97/03581

§ 371 Date: Jan. 7, 1999

§ 102(e) Date: Jan. 7, 1999

(87) PCT Pub. No.: WO98/01109

PCT Pub. Date: Jan. 15, 1998

(30) Foreign Application Priority Data

Jul. 8, 1996 (DE) ............................... 196 27 498

(51) Int. Cl.$^7$ ............... A61K 7/00; A61K 7/16; A61K 7/135; A61K 7/06; A61K 7/11

(52) U.S. Cl. ............... 424/401; 424/49; 424/62; 424/70.1; 424/70.13; 424/489; 424/499; 510/109; 514/778; 514/844; 514/944

(58) Field of Search ................... 424/401, 489, 424/499, 49, 62, 70.1, 70.13; 514/778, 844, 944; 510/109

(56) References Cited

U.S. PATENT DOCUMENTS

| | | | |
|---|---|---|---|
| 3,137,592 | 6/1964 | Protzman et al. | 127/32 |
| 3,870,527 | * 3/1975 | Kryger et al. | 106/2 |
| 3,951,947 | * 4/1976 | Schanefelt et al. | 536/106 |
| 4,059,458 | 11/1977 | Germino et al. | 106/213 |
| 4,280,851 | 7/1981 | Pitchon et al. | 127/33 |
| 4,341,809 | * 7/1982 | Leshik et al. | 426/576 |
| 4,362,755 | * 12/1982 | Mitchell et al. | 426/579 |
| 4,508,705 | 4/1985 | Chaudhuri et al. | 424/47 |
| 4,600,472 | 7/1986 | Pitchon et al. | 159/4.4 |
| 4,865,867 | * 9/1989 | Platt et al. | 426/603 |
| 4,985,082 | 1/1991 | Whistler | 127/33 |
| 5,126,334 | 6/1992 | Fitt et al. | 514/60 |
| 5,149,799 | 9/1992 | Rubens | 536/102 |
| 5,279,313 | 1/1994 | Clausen et al. | 132/208 |
| 5,352,284 | * 10/1994 | Anic et al. | 106/162.81 |
| 5,496,861 | 3/1996 | Rouse et al. | 514/778 |
| 5,773,256 | 6/1998 | Pelenc et al. | 435/74 |
| 5,871,756 | * 2/1999 | Jeffcoat et al. | 424/401 |

FOREIGN PATENT DOCUMENTS

| | | |
|---|---|---|
| 249 912 | 9/1987 | (DE) . |
| 55-127308 | 10/1980 | (JP) . |
| 56-147622 | 11/1981 | (JP) . |
| 63-62535 | 3/1988 | (JP) . |
| 92066778 | 4/1992 | (WO) . |

OTHER PUBLICATIONS

R.E. Faust, "Starches in Topical Preparations", American Perfumer and Cosmetics, vol. 78, Oct. 1963, pp. 51–54.

* cited by examiner

Primary Examiner—Shelley A. Dodson
Assistant Examiner—Marina Lamm
(74) Attorney, Agent, or Firm—Karen G. Kaiser

(57) ABSTRACT

A composition for cleaning or caring for the skin, teeth or hair or for cleaning smooth surfaces in described, which has an aqueous phase containing a pregelatinized, crosslinked starch selected from a $C_2$–$C_5$ hydroxyalkyl starch and a $C_2$–$C_{18}$ acyl starch. Preference is given to hydroxypropyl di-starch phosphate or di-starch $C_4$–$C_{18}$-alkanoate or alkenoate. The starch acts 1) as a stability improver, 2) as a viscosity regulator, 3) as a (co)emulsifier, 4) as a skin feel improving agent and 5) as an agent for improving hairdressing characteristics.

28 Claims, No Drawings

STARCHY CLEANING AND COSMETIC CARE PREPARATIONS

BACKGROUND OF THE INVENTION

The present invention relates to compositions for cleaning or caring for the skin, teeth or hair, as well as for cleaning smooth surfaces. Consequently the invention relates to compositions which are intended to come or can come in contact with human skin.

Humectant characteristics, tactile characteristics giving a soft feel to the skin and lips, and a smooth, easily spreadable texture are sought in cosmetics. In conventional cosmetic compositions the tactile characteristics are provided by hydrophobic constituents such as waxes, oils and fats.

Improved humectant characteristics are obtained by adding to the composition hydrophilic constituents and forming a stable water-in-oil emulsion. The prior art emulsion-like compositions suffer from various disadvantages, e.g., lack of emulsion stability and high ingredient costs (e.g., hyaluronic acid), particularly in cream, lotion and beauty soap compositions.

The prior art discloses cosmetics which contain certain starches for overcoming these disadvantages.

U.S. Pat. No. 5,279,313 describes a hair bleaching composition which contains a persulphate having a specific particle size and alkaline reacting salts. As water-soluble thickeners, the composition can contain starches. Examples include maize or corn starch, starch ethers, such as carboxymethyl starch, hydroxyethyl starch and ethyl starch. The products according to U.S. Pat. No. 5,279,313 do not have adequate viscosity, storage stability and use characteristics.

JP 63-62535 describes the production of a stabilizing emulsifier, for whose production lecithin and polyglycerol are emulsified in a starch hydrolyzate solution and modified starch and xanthan gum are added. The modified starch is e.g. hydroxypropyl di-starch phosphate, hydroxypropyl starch or di-starch phosphate. The emulsifier obtained is intended to be a gum Arabic replacement. The fields of use given are condiments, emulsified spices, flavours, pastries, dairy products and medicinals. JP 63-62535 contains no information regarding a possible use in cosmetic or cleaning compositions. The starches used in the examples are cooking starches.

U.S. Pat. No. 4,059,458 relates to oil-in-water emulsions for use in foods, pharmaceuticals and cosmetics which contain an ester of a starch with at least one aliphatic $C_2$–$C_4$ carboxylic acid. The ester has a degree of substitution of 0.05 to 1.0 and can optionally be modified, oxidized, crosslinked or pregelatinized. The starch esters are not hydrolysis-stable, particularly in formulations having an acidic pH. This leads to an undesired viscosity drop, phase separation and an unpleasant odor caused by free carboxylic acids.

WO 92/06778 discloses compositions containing a $C_{12}$–$C_{22}$ alcohol, an alkyl polyoside and optionally polyoside. The alkyl polyoside can inter alia incorporate glucose, saccharose, maltose, lactose, cellobiose and starch. The compositions are intended for use in cosmetics and pharmaceuticals.

WO 93/04185 describes the enzymatic, stereospecific preparation of alpha-glucosides from starch, maltodextrin or maltose. The alpha-glucosides can be further reacted in the presence of a lipase with a fatty acid, in which alpha-glucoside esters are obtained which are suitable as detergents, surfactants and emulsifiers in cosmetic or pharmaceutical compositions. The starch merely serves as a reservoir for glucose units and is decomposed to low molecular weight units.

DD 249 912 discloses starch derivatives which are prepared by etherifying a starch with a halogenated fatty acid and heating to 80 to 130° C. to form intermolecular ester bridges. The starch deriviatives are suitable as emulsion stabilizers in the pharmaceutical, cosmetic and foods industries. These products are not suitable for building up an increased viscosity.

JP 56-147622 describes an emulsifier composition which contains the monoesters of a fatty acid with a trihydric alcohol, as well as galactomannan, glucomannan and/or starch.

JP 55-127308 describes weak acid, emulsified cosmetics which contain an oil-like cosmetic material, cationic cellulose or cationic starch with a specific N-content, triethanol amine or triisopropanol amine, higher fatty acids and water.

The known starch-containing cosmetics and cleaning compositions suffer from numerous disadvantages. In cold water native starch is a insoluble biopolymer. Thus, when using native starch it is necessary to heat over a long time period when producing the composition in order to solubilize the starch. In addition, agglomeration can occur when the starch is incorporated in water or an aqueous base. Apart from these processing disadvantages, the known starch-containing products have disadvantages during use and e.g. have an unpleasant, sticky feel on the skin or undissolved particles give an unpleasant, rough feeling. In addition, problems can occur in connection with the storage stability, which can be manifested in a phase separation, retrogradation of the starch used or lack of odor stability.

Therefore, the problem to be solved by the invention is to provide starch-based compositions which do not suffer from the aforementioned disadvantages.

SUMMARY OF THE INVENTION

According to the invention, this problem is solved by a composition for cleaning or caring for the skin, teeth or hair or for cleaning smooth surfaces comprising an aqueous phase which contains a pregelatinized, crosslinked starch selected from a $C_2$–$C_5$ hydroxyalkyl starch and a $C_2$–$C_{18}$ acyl starch.

The starch to be used according to the invention must be crosslinked. Crosslinking of the starch chains can be achieved by suitable crosslinking agents, i.e., bifunctional compounds. A preferred crosslinking method is phosphorylation, in which the starch is reacted with phosphorous oxychloride, phosphorous pentoxide, and/or sodium trimetaphosphate. Two starch chains are crosslinked by an anionic P-O group. The anionic character of the crosslinking sites assists the emulsion-stabilizing action of the starch to be used according to the invention. A further preferred crosslinking method is by means of $C_4$–$C_{18}$ alkane or alkene dicarboxylic acids, preferably $C_4$–$C_8$ alkane dicarboxylic acids, and in particular adipic acid. The alkane or alkene dicarboxylic acid links two starch chains via ester bonds. It can be in straight or branched chain form. The derivatives are obtained, e.g., by reacting starch with the mixed anhydrides of dicarboxylic acid and acetic acid. Based on the dry starch, in general less than 0.1 wt. %, normally about 0.06 wt. %, crosslinking agent is used.

The nature of the modification of the starch to be used according to the invention is critical. In one embodiment, the starch is $C_2$–$C_5$ hydroxyalkyl starch. It is assumed that the formation of a hydroxyl group, which is bound to the starch backbone via an alkyl group with 2 to 5 carbon atoms, leads to a suitable hydrophilic-lipophilic balance of the starch. The position of the hydroxyl group in the alkyl group is not critical and can be in the alpha to omega position. The degree of substitution of the hydroxyalkylation is preferably approximately 0.08 to 0.3. The degree of substitution is the average number of substituted OH groups of the starch molecule per anhydroglucose unit. The hydroxyalkylation of a native starch can be brought about by reacting a native starch with alkylene oxides with the appropriate number of carbon atoms. Particularly preferred are hydroxyethylated and/or hydroxypropylated starches obtained by reacting starches with ethylene oxide or propylene oxide. A starch to be used according to the invention can also contain more than one hydroxyl group per alkyl group.

In another embodiment the starch is a $C_2$–$C_{18}$ acyl starch. This starch regularly occurs if the aforementioned essential crosslinking has been brought about by $C_4$–$C_{18}$ alkanoate or alkenoate and can be additionally acylated with a view to a suitable hydrophilic-lipophilic balance with a degree of substitution of 0 to 0.8, particularly 0 to 0.5. Acylation generally takes place by reaction with acid anhydrides of general formula $(R-C(O))_2O$, in which R is an alkyl group, such as methyl or ethyl, with succinic or maleic anhydride or their alkylated derivatives.

A particularly preferred starch derivative for the purpose of the invention is a hydroxypropyl di-starch phosphate, as well as acetylated di-starch adipate.

The starch starting material can be derived from any plant source, but preferably the starch has an amylopectin content of at least about 70 wt. %, preferably about 85 wt. %, and in particular about 90 wt. %. Particularly preferred starches are derived from waxy maize.

A decisive feature of the invention is that the starch derivative to be used according to the invention is pregelatinized. Apart from the term "pregelatinized starch" the prior art also uses the terms "prepasted starch" and "cold water swelling starch". The term "pregelatinized" or "gelatinized" starch relates to swollen starch particles, which have lost their birefringence crosses in polarized light. Pregelatinized starches or starch derivatives are soluble in cold water without cooking. In this context "soluble" does not necessarily mean the formation of a true molecular solution and instead usually a colloidal dispersion is obtained. The starch derivative to be used according to the invention is preferably completely pregelatinized.

The process normally used for producing such pregelatinized starches are inter alia drum drying, extrusion and spray drying.

Drum drying includes the simultaneous cooking and drying of a very high viscosity, semi-solid starch paste on heated drums. The dried films are stripped from the drum with a metal blade and then ground. This process can be carried out up to a very high solids content.

It is also possible to use extrusion for the simultaneous cooking and drying of starches (cf. U.S. Pat. No. 3,137,592). This process makes use of the physical processing of a starch/water mixture at elevated temperatures and pressures which brings about the gelatinization of the starch, followed by expansion after leaving the nozzle with sudden evaporation of the water.

The use of pregelatinized starch derivative allows the production of the composition according to the invention at ambient temperature or at a temperature which is considerably lower than the production conditions used for known starch-containing compositions. It has surprisingly been found that with a cooking starch (i.e., non-gelatinized starch) modified in the same way as a starch to be used according to the invention, the desired advantages regarding rheology, skin feel and emulsion stability are not obtained even if the aqueous phase, following addition of the cooking starch, is heated for 15 minutes to a temperature above the gelatinizing temperature of the starch.

Preferably, the pregelatinized starch derivative is produced by spray drying. In other drying processes, e.g., drum drying, starch crusts can be formed which have an inferior solubility. This leads to undissolved particles in the composition according to the invention, which can give rise to an unpleasant, sandy feel on the skin.

Preferably, the starch derivative to be used according to the invention has a majority of intact starch granules. It has been found that the aqueous dispersions of pregelatinized starch derivatives having a largely intact granular structure have a more uniform smooth texture than aqueous dispersions of starches without a granular structure, which are, e.g., obtained by drying starch solutions whose dispersions have a slightly gritty feel. In the case of pregelatinized starches with an intact granular structure the native internal structure of the hydrogen bonds is destroyed, but the external shape or form is maintained.

A process for producing particularly suitable, spray dried, pregelatinized starches or starch derivatives is described in U.S. Pat. No. 4,280,851. An apparatus adapted for carrying out the process is described in U.S. Pat. No. 4,600,472. In this process a mixture of the granular starch or starch derivative is cooked or gelatinized in the atomized state. The starch to be cooked is atomized through an atomizing opening into a nozzle arrangement in order to form a relatively finely divided sprayed material. In addition, a heating medium is injected through an opening in the nozzle arrangement into the sprayed material so as to heat the starch to the temperature necessary for gelatinization. A closed chamber surrounds the injection openings for the atomizing and heating medium and defines a ventilation opening positioned in such a way that the heated starch spray material can leave the chamber. The arrangement is such that during the passage of the starch spray material through the chamber, i.e., from the atomizing opening to the ventilation opening, the time elapsed defines the starch's gelatinization time. The resulting spray dried, pregelatinized starch includes uniformly gelatinized starch granules in the form of indented spheres, most of the granules being whole and unbroken and swollen after hydration. Nozzles usable for producing such starches are also described in U.S. Pat. No. 4,610,760.

For the production of suitable pregelatinized starches or starch derivatives it is also possible to use the process of U.S. Pat. No. 5,149,799. In this process starch is uniformly atomized and cooked by means of a single atomization stage in the presence of an aqueous medium. The atomization stage is performed in an apparatus having an internal mix two-fluid spray drying nozzle and it is coupled to a device for drying the cooked, atomized starch.

Spray dried, pregelatinized starches or starch derivatives with suitable characteristics can also be produced by a continuous, coupled jet-cooking and spray-drying process. A starch suspension is gelatinized at 138 to 160° C. in a jet cooker with direct steam injection. The streams of starch suspension and steam are mixed in a cooking or boiling chamber. The outlet of the latter is connected to a pneumatic spray nozzle or a high pressure nozzle, which is located in a conventional spray dryer. The jet-cooked starch is directed at elevated temperature and pressure into the spray nozzle and can be atomized with cold air, hot air or preferably steam. After atomizing, the hot, jet-cooked starch solution is handled in the same way as conventional spray dried starches. The drying process is adequately fast to prevent retrogradation of the starch molecules during the cooling and drying of the droplets. The spray dried starch is an amorphous material (i.e., it is substantially non-crystalline) which is easily soluble in water or colloidally dispersible.

The composition according to the invention can be provided in any form, for example, as solution, emulsion, suspension, gel or foam. It can also be provided as a dry powdery composition which is reconstituted in an aqueous medium upon use. In general, the composition has preferably about 5 to 98%, particularly about 50 to 90 wt. %, of an aqueous phase. The aqueous phase preferably contains about 0.1 to 20 wt. %, particularly about 0.3 to 12 wt. %, and in a particularly preferred manner about 0.5 to 7 wt. %, of the starch derivative with the aforementioned features. The starch derivative to be used according to the invention can be used in conjunction with other starches, such as native starches, modified starches, and like starches.

In the composition according to the invention the inventively used starch derivative fulfils various functions. It acts 1) as a stability improver, 2) as a viscosity regulator, 3) as a (co)emulsifier, 4) as an agent for improving the skin feel, and 5) as an agent for improving hairdressing characteristics.

Aqueous dispersions of such starch derivatives are characterized by a variety of fat-like textures, which can range from oily, via creamy to waxy. These starch derivatives can be chosen in such a way that in aqueous dispersions starch gels of high strength or heat-reversible starch gels are obtained. A heat-reversible starch gel melts on heating and re-forms after cooling. Gels produced from unmodified starches are not heat-reversible. With the starches to be used according to the invention it is possible to wholly or partly replace oil or fat, and e.g., formulate oil-free lotions which have similar properties to oil-in-water emulsions.

The starch derivatives to be used according to the invention have use characteristics which are desirable from the dermatological standpoint. They increase the water retention capacity of the skin and make the latter smooth and flexible. Cosmetics containing a starch derivative to be used according to the invention can be spread very well onto the skin and do not leave behind a sticky feeling.

The starch derivatives to be used according to the invention have a stabilizing and oil-binding effect. They prevent the deposition of solid constituents, as well as the phase separation of liquid constituents. They also have a viscosity-raising effect and give the inventive composition a pleasing gloss. The starch derivatives to be used according to the invention also have a certain protective colloid action and consequently prevent the coalescing of emulsified droplets of a hydrophobic phase. Due to their action as a (co) emulsifier, it is possible to reduce the quantity of surface-active emulsifiers in the inventive cosmetics compared with conventional cosmetics. In certain cases there is no need for surface-active emulsifiers. Compared with other products, this offers advantages in cosmetics whose "natural" and "hyperallergenic" properties are stressed. The starch derivatives to be used according to the invention also have substantive characteristics, i.e., they can be drawn onto the human hair and make the latter more easily combable and sleek.

The oil-binding characteristics of the starch derivatives to be used according to the invention lead to an improved transport of oil-soluble active ingredients of the inventive cosmetics on the skin surface.

DESCRIPTION OF THE PREFERRED EMBODIMENTS

In a preferred embodiment the composition according to the invention contains at least about 0.3%, preferably about 7 to 25%, and in individual cases up to 70 wt. % surfactants. These compositions are in particular those in which a cleaning action is essential, e.g., shampoo, shower gel, foam bath, liquid soap, manual dishwashing composition or hair conditioning composition. Hereinafter these compositions are collectively referred to as WAS/starch combinations (WAS refers to washing-active substances).

The surfactants are preferably anionic, amphoteric and/or nonionic surfactants. Suitable anionic surfactants include alkali metal salts of alkyl sulfonates or sulfates with 8 to 22 carbon atoms in the alkyl chain. Sodium, ammonium, potassium or triethanol amine alkyl sulfates are preferred, particularly those obtained by the sulfation of higher alcohols (8 to 18 carbon atoms), as well as sodium salts of coconut oil fatty acid monoglyceride sulfates or sulfonates, sodium or potassium salts of sulphuric acid esters of adducts of 1 to 12 mole of ethylene oxide to higher fatty alcohols (e.g. tallow or coconut oil alcohols), sodium or potassium salts of alkyl phenol-ethylene oxide-ether sulfates with 1 to 10 ethylene oxide units per molecule, in which the alkyl radicals contain 8 to 12 carbon atoms, sodium alkyl glyceryl ether sulfonates, reaction products of $C_{10}$ to $C_{22}$ fatty acids, esterified with isethionic acid, sodium salt, water-soluble salts of condensation products of fatty acids with sarcosine. Further anionic surfactants are sulfoacetates and sulfosuccinates.

As amphoteric surfactants reference can be made to those constituting derivatives of aliphatic, quaternary ammonium, phosphonium and sulphonium compounds, in which the aliphatic radicals can be straight or branched and one of the aliphatic substituents contains 8 to 18 carbon atoms and one anionic group, e.g. a carboxylate, sulfonate, sulfate, phosphate or phosphonate group. Examples of these are 4-[N, N-di(hydroxyethyl)-N-octadecylammonio ]-butane-1-carboxylate, 5-S-hydroxypropyl-S-hexadecyl-sulfonio ]-3-hydroxypentane-1-sulfate, 3-[P,P-diethyl-P-3,6,9-trioxatetra-dioxylphosphonio ]-2-hydroxypropane-1-phosphate, 3-[N,N-dipropyl-N-3-dodecoxy-2-hydroxypropylammonio]-propane-1-phosphate, 3-(N,N-dimethyl-N-hexadecylammonio )-1-sulfonate, 3-(N, Ndimethyl-N-hexadecylammonio)-2-hydroxypropane-1-sulfonate, 4-[N,N-di(2-hydroxyldodecyl-ammonio]-butane-1 -carboxylate, 3-[S-ethyl-S-(3-dodecoxy-2-hydroxypropyl)-sulphonio]-propane-1-phosphate, 3-[P,P-dimethyl P-dodecyl-phosphonio]-propane-1-phosphonate and 5-[N,N-di(3-hydroxypropyl)-N-hexadecylammonio]-2-hydroxypentane-1-sulfate. Betaines are also suitable for the invention. Suitable betaines are inter alia the higher alkyl betaines, e.g. coconut dimethyl carboxymethyl betaine, lauryl dimethyl carboxymethyl betaine, lauryl dimethyl alpha-carboxyethyl betaine, cetyl dimethyl carboxymethyl methane, cetyl dimethyl carboxymethyl betaine, lauryl-bis (2-hydroxyethyl)-carboxymethyl betaine, stearly-bis(2-hyhdroxypropyl)-carboxymethyl betaine, oleyl dimethyl-gamma-carboxypropyl betaine, lauryl-bis(2-hydroxypropyl)-alpha-carboxyethyl betaine, etc., sulfobetaines, such as coconut dimethyl sulfopropyl betaine, stearyl dimethyl sulfopropyl betaine, lauryl dimethyl sulfo-ethyl betaine, lauryl-bis(2-hydroxyethyl)-sulfopropyl betaine, etc.; amido betaines and amidosulfo betaines, in which a $RCONH(CH_2)_3$ radical is connected to the betaine nitrogen atom are also suitable.

Nonionic surfactants, which are preferably used in combination with an anionic or amphoteric surfactant, can roughly be defined as compounds prepared by the condensation of an alkylene oxide on a hydrophobic organic compound. Examples of preferred classes of nonionic surfactants are polyethylene oxide condensates of alkyl phenols, e.g. the condensation products of alkyl phenols with 6 to 12 carbon atoms in the alkyl group with 10 to 60 mole ethylene oxide, condensation products of ethylene oxide with propylene oxide-ethylene diamine reaction products, condensation products of aliphatic alcohols with 8 to 18 carbon atoms with ethylene oxide, long-chain, tertiary amino oxides, long-chain, tertiary phosphine oxides, long-chain dialkyl sulfoxides. The term "long-chain" means that in the molecule there is at least one long hydrophobic chain which contains an alkyl, alkenyl, hydroxyalkyl or ketoalkyl radical with 8 to 20 carbon atoms. Other examples of nonionic surfactants are alkyl and alkenyl oligoglycosides, such as $C_{12}$–$C_{14}$ coconut alkyl oligoglucoside.

For hair care compositions and hair conditioning compositions, usually cationic compounds, preferably quaternary ammonium compounds, such as cetyl trimethyl ammonium chloride or diquaternary polydimethyl siloxanes, are used. The starch derivative to be used according to the invention shows the benefit of being compatible with cationic compounds, i.e., it remains dispersed in the presence of the cationic compound and maintains its viscosity.

The composition preferably has a pH-value between about 2.5 and 12, particularly between about 4 and 9. A desired pH-value is attained by adding suitable pH-regulators, such as citric acid, lactic acid, phosphoric acid, hydrochloric acid, sodium hydroxide, potassium hydroxide or triethanol amine. When using starch esters a strong acid pH-value should be avoided, because otherwise there is a hydrolysis of the ester bonds.

In a further embodiment, the composition according to the invention contains at least about 1 wt. %, particularly about 5 to 25 wt. %, and in individual cases up to 70 wt. % of a hydrophobic phase. The hydrophobic phase is preferably finely dispersed. The hydrophobic phase can correspond to the hydrophobic phase of conventional oil-in-water-based cosmetics and, e.g., contains liquid or solid fatty acid triglycerides, fatty acid monoesters or diesters, silicones and/or long-chain alcohols. These compositions are collectively referred to hereinafter as "emulsion-type" compositions.

To maintain the hydrophobic phase as fine dispersion, the emulsion-type compositions according to the invention preferably contain one or more additional emulsifiers, particularly a partial ester of a polyhydric alcohol, an ethoxylate, propoxylate and/or butoxylate having a HLB value of about 4 to 16 and/or ionic emulsifiers, such as citrates or tartrates of monoglycerides. It is also possible to use combinations of glycerin monostearate or distearate with fatty alcohol sulfates or alkali metal salts of fruit acid esters or glycerin mono- or difatty acid esters. The emulsifier is preferably about 0.1 to 10 and in particular about 0.5 to 5 wt. %. In this embodiment the inventive composition can be in the form of a cream, lotion or milk. As a function of the characteristics and quantity of the aqueous or hydrophobic phase, the emulsion-type compositions can contain different types of emulsions, e.g., binary oil-in-water or water-in-oil systems or multiple phase systems, such as water-in-oil-in-water or oil-in-water-in-oil systems.

In another preferred embodiment, the composition according to the invention is in the form of a high viscosity gel. The gel according to the invention preferably contains one or more monohydric or polyhydric alcohols, with particular preference being given to glycerin and/or ethanol. In the gel the alcohol is preferably present in a quantity of about 5 to 25 wt. %. A quantity of 25 wt. % should not be exceeded because otherwise the starch can precipitate. The gel can contain agents which give the skin a refreshing and cooling effect, such as e.g., menthol or menthyl lactate.

A further preferred embodiment of the invention is a hair dyeing or hair bleaching composition. These compositions are characterized by containing a colorant or an oxidizing agent, respectively. Generally, as oxidizing agents percompounds, such as peroxides, e.g., hydrogen peroxide, or persulfates are useful. The hair dyeing or hair bleaching composition can be provided as a one-component composition or preferably as a two-component composition. The two components of the composition are combined by the user prior to use and applied to the hair. If the composition is provided as two components, it is preferred that one component is powdery and the other component is liquid. The powdery component contains the starch derivative to be used according to the invention, and the liquid component contains an aqueous phase. Hair dyeing compositions or hair bleaching compositions generally have a high pH. Surprisingly, the starch derivative to be used according to the invention is stable also at the elevated pH of these products. The viscosity build up provided by the starch derivative to be used according to the invention enables the product to remain in place in the hair during use and enables the desired duration of exposure to be achieved. The starch to be used according to the invention can be easily dispersed in the aqueous medium without lumps. Polysaccharide thickening agents commonly used in hair treatment compositions, such as hydroxyethyl cellulose and xanthan gum, are typically difficult to disperse as they form clumps and fish-eyes.

For all the embodiments of the invention, as a function of the intended use, the composition according to the invention can contain additives selected from preservatives, perfumes, flavours, sun protection agents, antioxidants, vitamins, pharmaceutical active substances, fillers, sequestrants, colouring agents, bronzing agents, additional thickeners, inorganic salts, pH-regulators and/or pearlizing agents.

The composition according to the invention has numerous advantages. The starch raw materials are derived from renewable sources, which is in accordance with the composition behaviour of a increasing number of consumers. Starch raw materials have long been used in foods and can be looked upon as unobjectionable. Compared with conventionally used carbomers they contain no toxic monomers and no solvents. They also contain no pesticides, which can, e.g., be present in plant gums.

The invention will now be further illustrated by examples. The pH-values were measured electrometically in the undiluted product. The viscosity values were measured with a Haake type RV 20-Rotovisko viscometer with the measuring devices mentioned in the examples, following a one minutes shear time in accordance with DIN 53019. The batches or mixtures were produced on a 1 kg scale with a paddle agitator. Homogenization took place with a Fema AG type S 100 SL 90 homogenizer at stage 8 and with a holding time of 100 ml/min.

In the examples the following designations and trade names are used.

| Trade Name | Manufacturer | INCI Name |
|---|---|---|
| Dehyquart A | Henkel KGaA | Cetrimonium Chloride |
| Jaguar C-162 | Rhone-Poulenc | Hydroxypropyl Guar Hydroxypropyltrimonium Chloride |
| Lanette 14 | Henkel KGaA | Myristyl Alcohol |
| Tegopearl N 100 | TH. Goldschmidt AG | Glycol Distearate, Steareth-4 |
| Texapon N 70 | Henkel KGaA | Sodium Laureth Sulfate |
| Plantaren 1200 | Henkel KGaA | Lauryl Glucoside |
| Tego Betain F | TH. Goldschmidt AG | Cocamidopropyl Betaine |
| Elfan NS 242 A | Akzo Nobel | Sodium Laureth Sulfate |
| Tego Betaine F 50 | TH. Goldschmidt AG | Cocamidopropyl Betaine |
| Axol C62 | TH. Goldschmidt AG | Glyceryl Stearate Citrate |
| Nipagin | Nipa Laboratorien GmbH | Methylparaben |
| Nipasol | Nipa Laboratorien GmbH | Propylparaben |
| Prisorine 3700 | Unichema International | Polyglycerol-3 Diisostearate |
| Tegin 90 | TH. Goldschmidt AG | Glyceryl Stearate |
| Miglycol 812 | Huls AG | Caprylic/Capric Triglyceride |
| Sucro-Ester WE15 | Gattefosse GmbH | Sucrose Palmitate |
| Cetiol 868 | Henkel KGaA | Octyl Stearate |
| Phenonip | Nipa Laboratorien GmbH | Phenoxyethanol, Methylparaben, Butylparaben, Ethylparaben, Propylparaben |
| Parsol MCX | Givaudan-Roure | Octyl Methoxycinnamate |
| Uvinul MS 40 | BASF | Benzophenone-4 |
| Natrium-Hyaluronat | ROVI GmbH | Sodium Hyaluronate |
| Vitamin A-Palmitat | BASF AG | Retinyl Palmitate |
| Vitamin E Acetat | BASF AG | Tocopheryl Acetate |
| Ronoxan A | Hoffman La Roche AG | Ascorbylpalmitate, D,L-apha-Tocopherol, Lecithin |
| Tego Care 215 | TH. Goldschmidt AG | Ceteareth-15, Glyceryl Stearate |
| Tego Care 450 | TH. Goldschmidt AG | Polyglyceryl-3 Methylglucose Distearate |
| Protegin | TH. Goldschmidt AG | Mineral Oil, Petrolatum, Ozokerite, Glyceryl Oleate, Lanolin Alcohol |
| Neo PCL W/O E 2/066255 | Dragoco Gerberding & Co. AG | Cetearyl Octanoate, Ceresin, Lanolin, Sorbitan Sesquioleate, Stearyl Heptanoate, Paraffinum liquidum, Trihydroxystearin, BHT |
| Hydroviton | Dragoco Gerberding & Co. AG | Aqua, Sodium Lactate, Lactic Acid, Glycerin, Serine, Sorbitol, TEA Lactate, Triethanolamine, Urea, Sodium Chloride, Lauryl Diethylenediaminoglycerine, Allantoin: Lauryl Aminopropylglycerine, Alcohol |
| Texapon ALS | Henkel KgaA | Ammonium Lauryl Sulfate |
| Rewopol SBFA | Witco Surfactants GmbH | Disodium Laurethsulfosuccinate |
| Euxyl K400 | Schulke & Mayr | Methyldibromo Glutaronitril, Phenoxyethanol |
| Sident 12DS | Degussa | Silica |
| Texapon K1296 Pulver | Henkel KgaA | Ammonium Lauryl Sulfate |
| Rewopol SBFA | Witco Surfactants GmbH | Disodium Laurethsulfosuccinate |
| Euxyl K400 | Schulke & Mayr | Methyldibromo Glutaronitril, Phenoxyethanol |
| Sident 12DS | Degussa | Silica |
| Texapon K1296 Pulver | Henkel KgaA | Sodium Lauryl Sulfate |
| Saccharin Na | Bayer AG | Sodium Saccharin |
| Cutina FS 45 | Henkel KgaA | Palmitic Acid, Stearic Acid |
| Luviskol K30 | BASF AG | PVP |
| Cyclodextrin Beta W7 | Wacker GmbH | Cyclodextrin |
| Pionier 4656 | Hansen & Rosenthal | Mineral Oil |
| Vaseline | Hansen & Rosenthal | Petrolatum |
| Titandioxid | Les Colorants Wackherr S.A. | |

EXAMPLES

Examples 1 to 3

These examples illustrate the preparation of a hair rinse using the following formulation:

| Raw Materials | Example 1 wt. % | Example 2 wt. % | Example 3 (control) wt. % |
|---|---|---|---|
| Water | 87.050 | 87.050 | 89.750 |
| Dehyquart A | 3.000 | 3.000 | 3.000 |
| Jaguar C-162 | 0.500 | 0.500 | 0.500 |
| Pregelatinized, hydroxypropylated di-starch phosphate of waxy maize starch in the form of loosely agglomerated granules | 2.700 | — | — |
| Hydropropylated di-starch phosphate of tapioca starch* | — | 2.700 | — |
| Lanette 14 | 3.000 | 3.000 | 3.000 |
| Tegopearl N 100 | 3.000 | 3.000 | 3.000 |
| Perfume | 0.400 | 0.400 | 0.400 |

-continued

| Raw Materials | Example 1 wt. % | Example 2 wt. % | Example 3 (control) wt. % |
|---|---|---|---|
| Citric Acid | 0.050 | 0.050 | 0.050 |
| Benzoic Acid | 0.300 | 0.300 | 0.300 |
| Specification values for: | | | |
| pH | 5.1 | 5.2 | 5.1 |
| Viscosity MV stage 1 (mpas) | 5100 | 1350 | 1100 |

*Farinex VA 70T (Avebe/Stadex, Malmo, Sweden)

Into the water heated to about 55° C. were stirred Dehyquart A, benzoic acid and the starch derivatives (except for Example 3 which contained no starch). When this mixture was homogenized, Jaguar C-162 and citric acid were stirred in. Lanette 14 which contained no starch was heated to 55° C. and stirred into the mixture. After cooling to about 40° C., accompanied by stirring, Tegopearl N 100 and the perfume were added to the mixture. After cooling to about 25° C., accompanied by stirring, a medium-viscosity, pearly bright dispersion was obtained in Example 1. Examples 2 and 3 were too watery and could not be used.

In use tests on normal damaged hair, the hair rinse according to Example 1 was given a good evaluation. Poor results were obtained with Examples 2 and 3 with regards to their dispersibility on wet hair and wet combability.

The storage tests for Example 1 at −18° C., +4° C., ambient temperature (18 to 25° C.), +30° C. and +40° C. after one month revealed a product substantially unchanged compared with the specifications. Phase separation occurred after one day with Examples 2 and 3.

Examples 4 to 6

These examples illustrate the preparation of a shampoo, using the following formulation:

| Raw material | Example 4 wt. % | Example 5 wt. % | Example 6 (control) wt. % |
|---|---|---|---|
| Water | 73.21 | 73.21 | 73.81 |
| Texapon N 70 | 11.00 | 11.00 | 11.00 |
| Plantaren 1200 | 3.50 | 3.50 | 3.50 |
| Sodium benzoate | 0.40 | 0.40 | 0.40 |
| Citric acid | 0.49 | 0.49 | 0.49 |
| Potassium Sorbate | 0.20 | 0.20 | 0.20 |
| Tego Betaine F | 4.20 | 4.20 | 4.20 |
| Sodium chloride, 22% solution in water | 6.00 | 6.00 | 6.00 |
| D-Panthenol | 0.10 | 0.10 | 0.10 |
| Pregelatinized, hydroxypropylated di-starch phosphate of waxy maize starch in the form of loosely agglomerated granules | 0.60 | — | — |
| Hydroxypropylated di-starch phosphate of potato starch* | — | 0.60 | — |
| Perfume | 0.30 | 0.30 | 0.30 |
| Specification values for: | | | |
| pH | 5.0 | 5.1 | 5.2 |
| Viscosity NV stage 1 (mpas) | 11100 | 7200 | 7000 |

*Farinex VA 70 (Avebe/Stadex, Malmo, Sweden)

Into the water at about 25° C. were successively stirred Plantaren 1200, sodium benzoate, potassium sorbate, citric acid, Tego Betaine F, D-Panthenol and the starch derivatives (except for Example 6 which contained no starch). When the mixture became homogeneous, the 22% sodium chloride solution was stirred in. Accompanied by vigorous stirring Texapon N 70 was added. The perfume was stirred in when the mixture became homogenous.

According to Example 4 a slightly opalescent, viscous shampoo was obtained. Example 5 and 6 had a much too low viscosity.

When used on hair, the shampoo according to Example 4 had good wet combability characteristics, besides a finebubble foam. Examples 5 and 6 formed a much larger bubble foam than Example 4 on the hair and the wet comability was inferior.

The storage tests for the product according to Example 4 at −18° C., +4° C., ambient temperature (18 to 25° C.) and +30° C. after one month revealed a product largely unchanged compared with the specifications. Example 5 showed phase separation after two days at ambient temperature.

The viscosity of Example 4 was in fact higher than the indicated value because the measuring range of the viscosimeter used was exceeded.

Example 7 to 9

These examples illustrate the preparation of foam bath using the following formulation:

| Raw material | Example 7 wt. % | Example 8 wt. % | Example 9 (control) wt. % |
|---|---|---|---|
| Elfan NS 242 A | 89.38 | 89.38 | 90.08 |
| Glycerin (87%) | 2.72 | 2.72 | 2.72 |
| Tego betaine F50 | 3.00 | 3.00 | 3.00 |
| Plantaren 1200 | 2.00 | 2.00 | 2.00 |
| Potassium sorbate | 0.20 | 0.20 | 0.20 |
| Sodium benzoate | 0.40 | 0.40 | 0.40 |
| Citric acid | 0.80 | 0.80 | 0.80 |
| Pregelatinized, hydroxypropylated di-starch phosphate of waxy maize starch in the form of loosely agglomerated granules | 0.70 | — | — |
| Hydroxypropylated di-starch phosphate of potato starch* | — | 0.70 | — |
| Perfume | 0.80 | 0.80 | 0.80 |
| Specification values for: | | | |
| pH | 5.0 | 5.1 | 4.9 |
| Viscosity MV stage 1 20° C. (mpas) | 14500 | 7500 | 7200 |

*Farinex VA 70 (Avebe/Stadex, Malmo, Sweden)

Into the Elfan NS 242 A at about 25° C. were successively stirred Plantaren 1200, sodium benzoate, potassium sorbate, citric acid, Tego betaine F 50 and its starch derivatives (except for Example 9 which contained no starch derivative). The perfume was added, accompanied by stirring, when the mixture became homogeneous.

Example 7 gave a slightly opalescent, viscous foam bath with pleasant use characteristics. In bath water foams both of Examples 8 and 9 give a larger-bubble foam than Example 7. In addition, the bath foam of Example 8 gave a negative, sandy skin feel.

The storage tests for the product of Example 7 at −18° C., +40° C., ambient temperature (18 to 25° C.) and +30° C. after one month revealed a product largely unchanged compared with the specifications.

After storing for two days at ambient temperature, phase separation occurred with the product of Example 8.

Examples 10 to 15

These examples illustrate the preparation of an O/W body lotion using the following formulation:

| Raw material | Example 10 wt. % | Example 11 wt. % | Example 12 wt. % | Example 13 (control) wt. % |
|---|---|---|---|---|
| Water | 76.54 | 76.54 | 76.54 | 79.54 |
| Axol C62 | 3.00 | 3.00 | 3.00 | 3.00 |
| D-Panthenol | 0.25 | 0.25 | 0.25 | 0.25 |
| 87% glycerin | 3.00 | 3.00 | 3.00 | 3.00 |
| Pregelatinized, hydroxypropylated acetylated di-starch phosphate of waxy maize starch in the form of loosely agglomerated granules | 3.00 | — | — | — |
| Pregelatinized, waxy maize starch acetate, crosslinked with adipic acid-acetic acid anhydride in the form of loose, agglomerated granules | — | 3.00 | — | — |
| Pregelatinized, hydroxypropylated di-starch phosphate of tapioca starch, granular | — | — | 3.00 | — |
| Nipagin | 0.50 | 0.50 | 0.50 | 0.50 |
| Nipasol | 0.15 | 0.15 | 0.15 | 0.15 |
| Refined soy oil | 4.00 | 4.00 | 4.00 | 4.00 |
| Refined coconut oil | 8.00 | 8.00 | 8.00 | 8.00 |
| Prisorine 3700 | 0.70 | 0.70 | 0.70 | 0.70 |
| Vitamin E acetate | 0.01 | 0.01 | 0.01 | 0.01 |
| Jojoba oil | 0.50 | 0.50 | 0.50 | 0.50 |
| Perfume | 0.35 | 0.35 | 0.35 | 0.35 |
| Specification value for: | | | | |
| pH | 5.3 | 5.2 | 5.2 | 5.3 |
| Viscosity MV after 1 day (mpas) | 1250 | 1150 | 660 | 150 |

| Raw material | Example 14 wt. % | Example 15 wt. % |
|---|---|---|
| Water | 76.54 | 76.74 |
| Axol C62 | 3.00 | 3.00 |
| D-Panthenol | 0.25 | 0.25 |
| Glycerin (87%) | 3.00 | 3.00 |
| Pregelatinized, hydroxpropylated di-starch phosphate of waxy maize starch in the form of loosely agglomerated granules | 3.00 | 3.00 |
| Nipagin | 0.50 | 0.50 |
| Nipasol | 0.15 | 0.15 |
| Miglycol 812 | 4.00 | 4.00 |
| Paraffin oil | 8.00 | 8.00 |
| Prisorine 3700 | 0.70 | |
| Tegin 90 | | 0.50 |
| Vitamin E acetate | 0.01 | 0.01 |
| Jojoba oil | 0.50 | |
| Cetiol 868 | | 0.50 |
| Perfume | 0.35 | 0.35 |
| Specification values for: | | |
| pH | 5.1 | 5.5 |
| Viscosity MV after 1 day (mpas) | 1250 | 2500 |

Axol C62, the starch derivatives (except for Example 13 which contained not starch deriative), Nipagin, Nipasol were heated, accompanied by stirring, at 75° C. in ⅔ of the total water quantity until the mixture was homogeneous, followed by the addition of D-Panthanol and 87% glycerin to the mixture. The coconut oil, soy oil, Prisorine 3700 or Tegin 90 and vitamin E acetate were heated to about 60° C. and added to the water phase, accompanied by stirring. When this mixture was homogeneous, the remaining quantity of the water at about 20° C. was added to the mixture, accompanied by stirring. The perfume was added, accompanied by stirring, at about 40° C. The mixture was then homogenized with a homogenizer and stirred on to about 25° C.

When used on the skin, the emulsions according to Examples 10, 11, 12, 14 and 15 had an excellent skin feel. The emulsion according to Example 13 was evaluated as having no content.

The storage tests for Examples 10, 11, 12, 14 and 15 at −18° C., +4° C., ambient temperature (18 to 25° C.), +30° C. and +40° C revealed that after 3 months storage of the product were largely unchanged compared with the specifications. After prolonged storage, the lotion according to Example 11 had a slightly acid odor.

At all the storage temperatures the emulsion according to Example 13 separated after at the latest two days.

Examples 16 to 18

These examples illustrate the preparation of an O/W cosmetic cream using the following formulation:

| Raw material | Example 16 wt. % | Example 17 wt. % | Example 18 (control) wt. % |
|---|---|---|---|
| Water | 55.735 | 55.735 | 60.735 |
| Nipagin | 0.350 | 0.350 | 0.350 |
| Nipasol | 0.150 | 0.150 | 0.150 |
| D-Panthenol | 0.200 | 0.200 | 0.200 |
| Vitamin E acetate | 0.500 | 0.500 | 0.500 |
| Glycerin (87%) | 5.000 | 5.000 | 5.000 |
| Sucro-ester WE 15 | 2.000 | 2.000 | 2.000 |
| Axol C 62 | 2.000 | 2.000 | 2.000 |
| Prisorine 3700 | 0.700 | 0.700 | 0.700 |
| Perfume | 0.100 | 0.100 | 0.100 |
| Refined coconut fat | 18.000 | 18.000 | 18.000 |
| Pregelatinized, hydroxypropylated di-starch phosphate of waxy maize starch in the form of loosely agglomerated granules | 5.000 | — | — |
| Hydroxypropylated di-starch phosphate of tapioca starch* | — | 5.000 | — |
| Refined soy oil | 8.000 | 8.000 | 8.000 |
| Sodium hyaluronate | 0.005 | 0.005 | 0.005 |
| Vitamin A-palmitate | 0.060 | 0.060 | 0.060 |
| Ronoxan A | 0.200 | 0.200 | 0.200 |
| Jojoba oil | 2.000 | 2.000 | 2.000 |
| Specification values for: | | | |
| pH | 5.1 | 5.5 | 5.3 |
| Viscosity SV stage 4 (20° C.) | 6640 | too low viscosity, not measurable | too low viscosity, not measurable |

*Farinex VA 70T (Avebe/Stadex, Malmo, Sweden)

The starch derivatives (except for Example 18 where not starch derivative was present) were stirred in water for about 10 minutes at 80° C., followed by the addition to the mixture, accompanied by stirring, of Sucro-ester WE 15 and Axol C62, and then D-Panthenol, Nipagin, Nipasol and glycerin. The coconut oil, soy oil, Prisorine 3700 and vitamin E acetate were separately heated to about 60° C. and added to the water phase, accompanied by stirring. Accompanied by stirring, the mixture is cooled to about 40° C. and sodium hyaluronate, vitamin A-palmitate, Ronoxan A, jojoba oil and perfume were added, accompanied by stirring. The mixture was then homogenized with a homogenizer and stirred on to about 25° C.

The cream according to Example 16 has excellent cosmetic properties when used on the skin. The evaluation of the cream of Example 17 was much inferior. The product of Example 18 become inhomogeneous shortly after application to the skin.

The storage tests of the cream according to Example 16 at −18° C., +4° C., ambient temperature (18 to 25° C.), +30°

C. and +40° C. revealed a substantially unchanged product after 3 months. Examples 17 and 18, after 3 days under all test conditions, revealed inhomogeneities.

Examples 19 to 21

These examples illustrate the preparation of an alcohol-containing lotion with a deodorant action using the following formulation:

| Raw material | Example 19 wt. % | Example 20 wt. % | Example 21 (control) wt. % |
|---|---|---|---|
| Water | 60.24 | 60.24 | 62.24 |
| Axol C62 | 3.00 | 3.00 | 3.00 |
| Pregelatinized, hydroxypropylated di-starch phosphate of waxy maize starch in the form of loosely agglomerated granules | 2.00 | — | — |
| Hydroxypropylated di-starch phosphate of tapioca starch* | — | 2.00 | — |
| D-Panthenol | 0.40 | 0.40 | 0.400 |
| Triethyl citrate | 1.00 | 1.00 | 1.00 |
| Farnesol | 0.50 | 0.50 | 0.50 |
| Prisorine 3700 | 0.56 | 0.56 | 0.56 |
| Glycerin (87%) | 3.00 | 3.00 | 3.00 |
| Perfume | 0.80 | 0.80 | 0.80 |
| Refined soy oil | 8.50 | 8.50 | 8.50 |
| Specification values for: | | | |
| pH | 5.5 | 5.2 | 5.4 |
| Viscosity SV stage 4 (mpas) | 700 | 150 | 120 |

*Farinex VA 70 (Avebe/Stadex, Malmo, Sweden)

The starch derivatives (except for Example 21 where no starch derivative was used) were strewn in water at 80° C., stirred for about 10 min and then Axol C62 was added to the mixture, accompanied by stirring, followed by D-Panthanol and glycerin. The soy oil and Prisorine 3700 were separately heated to about 60° C. and added to the aqueous phase, accompanied by stirring. Accompanied by stirring cooling took place to about 40° C. and ethanol, triethyl citrate, Farnesol and perfume were added, accompanied by stirring. The mixture was then homogenized with a homogenizer and stirred on to about 25° C.

When used on the skin, a positive evaluation with regards to its use characteristics was given to the lotion of Example 19. Examples 20 and 21 were considered to have less content or be watery. Example 20 was also considered to be sandy.

The storage tests on Example 19 at −18° C., +4° C., ambient temperature (18 to 25° C.), +30° C. and +40° C. revealed a substantially unchanged product after 3 months.

However, the products of Examples 20 and 21 revealed phase separation at ambient temperature after 1 day.

Examples 22 to 24

These examples illustrate the preparation of an alcohol-containing cream with light protection action.

| Raw material | Example 22 wt. % | Example 23 wt. % | Example 24 (control) wt. % |
|---|---|---|---|
| Water | 47.40 | 47.40 | 49.80 |
| Axol C62 | 3.20 | 3.20 | 3.20 |
| Uvinul MS 40 | 2.00 | 2.00 | 2.00 |
| Parsol MCX | 3.00 | 3.00 | 3.00 |
| Pregelatinized, hydroxypropylated di-starch phosphate of waxy maize starch in the form of loosely agglomerated granules | 2.40 | — | — |
| Hydroxypropylated di-starch phosphate of potato starch* | — | 2.40 | — |
| D-Panthenol | 0.40 | 0.40 | 0.40 |
| Prisorine 3700 | 0.56 | 0.56 | 0.56 |
| Avocado oil | 0.80 | 0.80 | 0.8 |
| Jojoba oil | 0.80 | 0.80 | 0.80 |
| Glycerin (87%) | 3.20 | 3.20 | 3.20 |
| Perfume | 3.20 | 3.20 | 3.20 |
| 94.5 wt. % ethanol | 20.00 | 20.00 | 20.00 |
| Refined coconut oil | 16.00 | 16.00 | 16.00 |
| Specification values for: | | | |
| pH | 5.4 | 5.3 | 5.4 |
| Viscosity M stage 4 (mpas) | 3200 | 1100 | 800 |

*Farinex VA 70 (Avebe/Stadex, Malmo, Sweden)

The starch derivatives (except for in Example 24 where no starch derivative was used) were strewn into the water at 80° C., stirred for about 10 min., followed by the addition to the mixture of Axol C62, accompanied by stirring and then followed by Uvinul MS 40, D-Panthenol and glycerin. The coconut oil, avocado oil, jojoba oil, Parsol MCX and Prisorine 3700 were separately heated to about 60° C. and added to the aqueous phase, accompanied by stirring. Accompanied by stirring, cooling took place to about 40° C. and ethanol and perfume were added, accompanied by stirring. The mixture was homogenized with a homogenizer and stirred on to about 25° C.

The use characteristics of the product of Example 22 were assessed as good.

The storage tests at −18° C., +4° C., ambient temperature (18 to 25° C.), +30° C. and +40° C. revealed a largely unchanged product after 3 months.

The use characteristics of the products according to Examples 23 and 24 were considered to be less satisfactory. Example 23 also gave a sandy impression.

The products of Examples 23 and 24 suffered phase separation after 1 day.

Examples 25 to 34

These examples illustrate the preparation of an O/W body lotion using the following formulation:

| Raw material | Example 25 wt. % | Example 26 wt. % | Example 27 wt. % | Example 28 wt. % |
|---|---|---|---|---|
| Water | 76.54 | 76.54 | 76.54 | 79.54 |
| Axol C62 | 3.00 | 3.00 | 3.00 | 3.00 |
| D-Panthenol | 0.25 | 0.25 | 0.25 | 0.25 |
| Glycerin (87%) | 3.00 | 3.00 | 3.00 | 3.00 |
| Maize starch, modified with octenyl succinanhydride, acid-treated | 3.00 | — | — | — |

-continued

| | | | | |
|---|---|---|---|---|
| Pregelatinized maize starch, drum dried | — | 3.00 | — | — |
| Pregelatinized maize starch, granular | — | — | 3.00 | — |
| Pregelatinized waxy maize starch | — | — | — | 3.00 |
| Nipagin | 0.50 | 0.50 | 0.50 | 0.50 |
| Nipasol | 0.15 | 0.15 | 0.15 | 0.15 |
| Refined soy oil | 4.00 | 4.00 | 4.00 | 4.00 |
| Refined coconut oil | 8.00 | 8.00 | 8.00 | 8.00 |
| Prisorine 3700 | 0.70 | 0.70 | 0.70 | 0.70 |
| Vitamin E acetate | 0.01 | 0.01 | 0.01 | 0.01 |
| Jojoba oil | 0.50 | 0.50 | 0.50 | 0.50 |
| Perfume | 0.35 | 0.35 | 0.35 | 0.35 |
| Specification values for: | | | | |
| pH | 5.6 | 5.5 | 5.7 | 5.6 |
| Viscosity MV (mpas) | 125 | 180 | 200 | 250 |

| Raw material | Example 29 wt. % | Example 30 wt. % | Example 31 wt. % | Example 32 wt. % |
|---|---|---|---|---|
| Water | 76.54 | 76.54 | 76.54 | 79.54 |
| Axol C62 | 3.00 | 3.00 | 3.00 | 3.00 |
| D-Panthenol | 0.25 | 0.25 | 0.25 | 0.25 |
| Glycerin (87%) | 3.00 | 3.00 | 3.00 | 3.00 |
| Thin-boiling, hydroxypropylated maize starch | 3.00 | — | — | — |
| Hydroxypropylated di-starch phosphate of waxy maize starch | — | 3.00 | — | — |
| Hydroxypropylated di-starch phosphate | — | — | 3.00 | — |
| Hydroxypropylated di-starch phosphate of maize starch | — | — | — | 3.00 |
| Nipagin | 0.50 | 0.50 | 0.50 | 0.50 |
| Nipasol | 0.15 | 0.15 | 0.15 | 0.15 |
| Refined soy oil | 4.00 | 4.00 | 4.00 | 4.00 |
| Refined coconut oil | 8.00 | 8.00 | 8.00 | 8.00 |
| Prisorine 3700 | 0.70 | 0.70 | 0.70 | 0.70 |
| Vitamin E acetate | 0.01 | 0.01 | 0.01 | 0.01 |
| Jojoba oil | 0.50 | 0.50 | 0.50 | 0.50 |
| Perfume | 0.35 | 0.35 | 0.35 | 0.35 |
| Specification values for: | | | | |
| pH | 5.1 | 5.2 | 5.4 | 5.0 |
| Viscosity MV stage 4 (mpas) | | | 1010 | |

| Raw material | Example 33 wt. % | Example 34 wt. % |
|---|---|---|
| Water | 76.54 | 76.74 |
| Axol C62 | 3.00 | 3.00 |
| D-Panthenol | 0.25 | 0.25 |
| Glycerin (87%) | 3.00 | 3.00 |
| Hydroxpropylated di-starch phosphate of potato starch* | 3.00 | — |
| Hydroxypropylated di-starch phosphate of tapioca starch** | — | 3.00 |
| Nipagin | 0.50 | 0.50 |
| Nipasol | 0.15 | 0.15 |
| Refined soy oil | 4.00 | 4.00 |
| Refined coconut oil | 8.00 | 8.00 |
| Prisorine 3700 | 0.70 | 0.70 |
| Vitamin E acetate | 0.01 | 0.01 |
| Jojoba oil | 0.50 | 0.50 |
| Perfume | 0.35 | 0.35 |
| Specification values for: | | |
| pH | 5.6 | 5.6 |
| Viscosity KV (mpas) | 60 | 50 |

*Farinex VA 70 (Avebe/Stadex, Malmo, Sweden)
**Farinex VA 70T (Avebe/Stadex, Malmo, Sweden)

Preparation took place as in Examples 10 to 15.

The storage stability was inadequate in Examples 25 to 32 and there was a clear phase separation after a short time. The mixtures of Examples 33 and 34 had a very limited, unusable viscosity for this product type. After 2 days a phase separation was detected at ambient temperature. A sandy skin feel was noted in use tests.

Examples 35 and 36

These examples illustrate the preparation of an O/W body cream, using the following formulation:

| Raw material | Example 35 wt. % | Example 36 wt. % |
|---|---|---|
| Water | 65.76 | 66.36 |
| Tego Care 215 | 3.00 | — |
| Tego Care 450 | — | 3.00 |
| Tegin 90 | 0.60 | — |
| D-Panthenol | 0.13 | 0.13 |
| Glycerin (87%) | 3.00 | 3.00 |
| Pregelatinized, hydroxpropylated di-starch phosphate of waxy maize starch in the form of loosely agglomerated granules | 5.00 | 5.00 |
| Phenonip | 0.90 | 0.90 |
| Vitamin A-palmitate | 0.06 | 0.06 |
| Refined soy oil | 10.00 | 10.00 |
| Refined coconut oil | 10.00 | 10.00 |
| Prisorine 3700 | 0.70 | 0.70 |
| Vitamin E acetate | 0.50 | 0.50 |
| Perfume | 0.35 | 0.35 |
| Specification values for: | | |
| pH | 7.0 | 7.2 |
| Viscosity MV (mpas) | 3800 | 4400 |

Pregelatinized, hydroxypropylated di-starch phosphate of waxy maize starch in the form of loose-agglomerated grains are heated, accompanied by stirring, at 80° C. in the water until the mixture is homogeneous, followed by the addition to the mixture of Phenonip, D-Panthenol and 87% glycerin and then the emulsifiers Tego Care 215 or Tego Care 450 were stirred in. The coconut oil, soy oil, Prisorine 3700, Tegin 90 and vitamin E acetate were heated to about 60° C. and added to the aqueous phase, accompanied by stirring. When the mixture was homogeneous, it was cooled, accompanied by stirring. At about 40° C. the perfume and vitamin A-palmitate are added, accompanied by stirring. The mixture was then homogenized with a homogenizer and stirred on to about 25° C.

The use characteristics of the product according to Examples 35 and 36 were considered to be good.

The storage tests at −18° C., +4° C., ambient temperature (18 to 25° C.), +30° C. and +40° C. revealed a largely unchanged product after 3 months.

Examples 37 to 39

These examples illustrate the preparation of a shaving foam using the following formulation:

| Raw material | Example 37 wt. % | Example 38 wt. % | Example 39 wt. % |
|---|---|---|---|
| Water | 73.922 | 73.922 | 74.422 |
| Propane/butane 3.5 bar | 5.000 | 5.000 | 5.000 |
| Eumulgin B2 | 1.000 | 1.000 | 1.000 |
| Gycerin (87%) | 8.730 | 8.730 | 8.730 |
| Pregelatinized, hydroxypropylated di-starch phosphate of waxy maize | 0.500 | — | — |

-continued

| Raw material | Example 37 wt. % | Example 38 wt. % | Example 39 wt. % |
|---|---|---|---|
| starch in the form of loosely agglomerated granules | | | |
| Hydroxypropylated di-starch phosphate of tapioca starch* | — | 0.500 | — |
| Cutina FS 45 | 5.277 | 5.277 | 5.277 |
| Myristic acid | 1.251 | 1.251 | 1.251 |
| Triethanol amine (min. 99%) | 3.030 | 3.030 | 3.030 |
| Luviskol K30 | 0.490 | 0.490 | 0.490 |
| Perfum | 0.800 | 0.800 | 0.800 |
| Specification values for: | | | |
| pH | 8.5 | 8.5 | 8.5 |
| Viscosity MV (mpas) | 1200 | 430 | 360 |

*Farinex VA 70T (Avebe/Stadex, Malmo, Sweden)

The starch derivative (except for in Example 39 where no starch derivative was used) was heated in the water at 75° C., accompanied by stirring, until the mixture was homogeneous, followed by the addition to the mixture of Cutina FS 45, myristic acid, Eumulgin B2 and 87% glycerin. After the fat components had melted, triethanol amine was added to the mixture, accompanied by stirring. After cooling to about 40° C., the perfume and Luviskol K30 were added, accompanied by stirring. The mixture was then homogenized with a homogenizer and stirred on to about 25° C. This active substance solution was filled into an aerosol can, the valve was fitted and the can was filled under pressure with the propellant propane/butane, after which the spray head was fitted to the can.

The use characteristics of the product according to Example 37 were evaluated as good. The products of Examples 38 and 39 were subject to a much poorer evaluation.

The storage tests the of product of Example 37 at −18° C., +4° C., ambient temperature (18 to 25° C.), +30° C. and +40° C. revealed a largely unchanged product after 3 months. The storage tests for the products of Examples 38 and 39 revealed phase separation under the same conditions after 7 days.

Examples 40 to 42

These examples illustrate the preparation of a W/O body cream using the following formulation:

| Raw material | Example 40 wt. % | Example 41 wt. % | Example 42 (control) wt. % |
|---|---|---|---|
| Water | 55.93 | 55.93 | 56.68 |
| Protegin | 20.00 | 20.00 | 20.00 |
| Epsom Salt | 0.30 | 0.30 | 0.30 |
| Glycerin (87%) | 2.00 | 2.00 | 2.00 |
| Pregelatinized, hydroxypropylated di-starch phosphate of waxy maize starch in the form of loosely agglomerated granules | 0.75 | — | — |
| Hydroxypropylated di-starch phosphate of tapioca starch* | — | 0.75 | — |
| Nipagin | 0.15 | 0.15 | 0.15 |
| Nipasol | 0.05 | 0.05 | 0.05 |
| Vitamin E acetate | 0.10 | 0.10 | 0.10 |
| Redefined coconut oil | 13.00 | 13.00 | 13.00 |

-continued

| Raw material | Example 40 wt. % | Example 41 wt. % | Example 42 (control) wt. % |
|---|---|---|---|
| Neo PCL W/O | 5.00 | 5.00 | 5.00 |
| Butyl hydroxytoluene | 0.02 | 0.02 | 0.02 |
| Hydroviton moisturizing factor | 2.00 | 0.50 | 0.50 |
| Perfume | 0.70 | 0.70 | 0.70 |
| Specification values for: | | | |
| pH | (1) | (1) | (1) |
| Viscosity SV stage 4 (mpas) | 21400 | 14300 | 15000 |

(1)–not measurable, because W/O system present
*Farinex VA 70T (Avebe/Stadex, Malmo, Sweden)

The starch derivative (except for in Example 42 where no starch derivative was used), Nipagin, Nipasol and Epsom salts were heated, accompanied by stirring, in the water quantity at 80° C. until the mixture was homogeneous, followed by the addition to the mixture of 87% glycerin. The coconut oil, Protegin, Neo PCL W/O and butyl hydroxytoluene were heated to about 75° C. and added to the aqueous phase, accompanied by stirring. When the mixture was homogeneous, it was cooled, accompanied by stirring. At about 40° C. the perfume, hydroviton moisturizing factor and vitamin E acetate were added, accompanied by stirring. The mixture was then homogenized with a homogenizer and stirred on to about 25° C. The use characteristics of the product of Example 40 were evaluated as good.

The storage tests at −18° C., +4° C., ambient temperature (18 to 25° C.), +30° C. and +40° C. revealed a largely unchanged product after 5 months.

The phase stability for the products of Examples 41 and 42 was not adequate.

Examples 43 to 45

These examples illustrate the preparation of a dishwashing composition using the following formulation:

| Raw material | Example 43 wt. % | Example 44 wt. % | Example 45 (control) wt. % |
|---|---|---|---|
| Water | 20.90 | 20.90 | 23.90 |
| Texapon ALS | 50.00 | 50.00 | 50.00 |
| Plantaren 1200 | 5.00 | 5.00 | 5.00 |
| Rewopol SBFA | 15.00 | 15.00 | 15.00 |
| Ethanol | 5.00 | 5.00 | 5.00 |
| Citric acid | 0.50 | 0.50 | 0.50 |
| Euxyl K400 | 0.20 | 0.20 | 0.20 |
| D-Panthenol | 0.10 | 0.10 | 0.10 |
| Pregelatinized, hydroxypropylated, acetylated di-starch phosphate of waxy maize starch in the form of loosely agglomerated granules | 3.00 | — | — |
| Hydroxypropylated di-starch phosphate of tapioca starch* | — | 3.00 | — |
| Perfume | 0.30 | 0.30 | 0.30 |
| Specification values for: | | | |
| pH | 5.5 | 5.4 | 5.7 |
| Viscosity MV (mpas) | 4200 | 1400 | 1200 |

*Farinex VA 70T (Avebe/Stadex, Malmo, Sweden)

Into the water at about 25° C. were successively stirred Texapon ALS, Plantaren 1200, Rewopol SBFA, Euxyl K400, citric acid and the starch derivatives (except for Example 45 where no starch was present). D-Panthenol, ethanol and perfume were stirred in when the mixture became homogeneous.

According to Example 43 a slightly opalescent, viscous dishwashing composition was obtained. The compositions of Examples 44 and 45 had a much lower viscosity.

In use, apart from a stable foam, the dishwashing composition had a good cleaning action and a good skin feel. The compositions of Examples 44 and 45 form a much larger-bubble foam than the composition of Example 43.

The storage tests of the product according to Example 43 at −18° C., +40° C., ambient temperature (18 to 25° C.) and +30° C. gave a largely unchanged product compared with the specifications after 1 month.

The composition of Example 44 revealed a phase separation at ambient temperature after 2 days.

Example 46

This example illustrates the preparation of a dental cream using the following formulation:

| Raw material | Example 46 wt. % |
| --- | --- |
| Water | 24.70 |
| Sodium hydrogen carbonate | 20.00 |
| Sident 12DS | 15.00 |
| Glycerin | 15.00 |
| Sorbitol (70%) | 10.00 |
| Sodium pyrophosphate | 4.00 |
| Sodium carbonate | 2.00 |
| Texapon K1296 powder | 2.00 |
| Pregelatinized, hydroxypropylated di-starch phosphate of waxy maize starch in the form of loosely agglomerated granules | 5.00 |
| Sodium saccharine | 0.10 |
| Sodium fluoride | 0.20 |
| Titanium dioxide | 1.00 |
| Flavor | 1.00 |
| Specification values for: | |
| pH | 9.0 |
| Viscosity MV (mpas) | 14500 |

Into the water at about 25° C. were successively stirred sodium hydrogen carbonate, sodium carbonate, sodium fluoride, the starch derivative, Sident 12DS, glycerin, 70% sorbitol, sodium pyrophosphate, Texapon K1296, sodium saccharine, titanium dioxide and flavor. Homogenization took place until the mixture is homogeneous.

According to Example 46, a white, high viscosity dental cream were obtained.

In use the dental cream gives a good cleaning action and a pleasant mouth feel, apart from a dense, stable foam.

The storage tests for the product according to Example 46 at −18° C., +4° C., ambient temperature (18 to 25° C) and +30° C. gave a largely unchanged product compared with the specifications after 1 month.

Example 47

This example illustrates the preparation of an emulsifier-free O/W body lotion using the following formulation:

| Raw material | Example 47 wt. % |
| --- | --- |
| Water | 77.700 |
| Cyclodextrin beta W7 | 1.000 |
| Glycerin (87%) | 5.000 |
| Pregelatinized, hydroxypropylated di-starch phosphate of waxy maize starch in the form of loosely agglomerated granules | 5.000 |
| Nipagin | 0.400 |
| Nipasol | 0.100 |
| Pionier 4656 | 5.000 |
| Vaseline | 5.000 |
| Titanium dioxide | 0.500 |
| Perfume | 0.300 |
| Specification values for: | |
| pH | 6.3 |
| Viscosity MV after 1 day (mpas) | 2250 |

The cyclodextrin, starch derivative, Nipagin, Nipasol and titanium dioxide were heated, accompanied by stirring, at 75° C. in ⅔ of the water until the mixture was homogeneous, followed by the glycerin addition. Pionier 4656 and Vaseline were heated to about 60° C. and added to the water phase. The remaining water quantity was then added. The perfume was added at 40° C. and the mixture was homogenized with a homogenizer. In use the body lotion had an excellent skin feel and was stable for at least six months.

Example 48

This example illustrates the preparation of a thickened hair bleaching system using the following formulations:

| Raw material | g |
| --- | --- |
| Component A | |
| Ammonium persulfate | 1,50 |
| Potassium hydrogen tartrate | 1,50 |
| Sodium carbonate | 1,50 |
| Sodium lauryl sulphate (Stepanol WA-100) | 0,50 |
| Hydroxypropylated distarch phosphate of waxy maize starch, pregelatinized according to US 4 280 851 | 0,75 |
| Magnesium hydroxide | 22,13 |
| Aluminum hydroxide | 22,12 |
| Component B | |
| Hydrogen peroxide 50% | 12,00 |
| Distilled water | 88,00 |

The ingredients of A were dry blended. The ingredients of B were mixed. For use, the two components were combined and applied to the hair. After combining, the hair bleaching composition had a viscosity of 30.219 mPas (Brookfield Heliopath, 10 rpm). For comparison, the identical formulation was prepared without the starch derivative. The composition had a viscosity of 431 mPas after blending.

Example 49

This example investigates the behaviour of different starch thickening agents in different environments. Each starch was added as a 10% solid dispersion to yield a 5% by weight final concentration in the following aqueous systems:
Condition:
1) Water
2) 2% $NH_4OH$
3) 2% $NH_4OH$ and 1% polymeric conditioning agent (Polyquaternium 6)

4) 2% NH$_4$OH and 1% monomeric conditioning agent (Cetrimonium chloride).

The 10% dispersions of the uncooked starches were prepared by boiling for 30 minutes while stirring. The 10% dispersions of the pre-gelatinized starches were prepared by mixing the starch into water at ambient temperature. The initial viscosities of the starch formulations and the viscosity development over time were recorded.

| Starch | Condition | Viscosity mPas, 45° C. |
|---|---|---|
| Spray-dried pregelatinized quaternized cross-linked waxy maize starch | 1 | 7400 |
|  | 2 | 2680 |
|  | 3 | 3040 |
|  | 4 | 2420 |
| Hydroxypropylated distarch phosphate waxy maize starch, uncooked high degree of substitution | 1 | 7892 |
|  | 2 | 14092 |
|  | 3 | 18092 |
|  | 4 | 7832 |
| Drum dried pre-gelatinized hydroxypropylated distarch phosphate waxy maize starch, moderate degree of substitution | 1 | 3100 |
|  | 2 | 5260 |
|  | 3 | 7940 |
|  | 4 | 1532 |
| Spray-dried pre-gelatinized hydroxypropylated distarch phosphate, waxy maize starch, moderate degree of substitution | 1 | 3452 |
|  | 2 | 12840 |
|  | 3 | 14132 |
|  | 4 | 2740 |
| Multicarboxylated potato starch, uncooked | 1 | 27472 |
|  | 2 | 25500 |
|  | 3 | 3732 |
|  | 4 | 0 |
| Hydroxypropylated waxy maize starch, uncooked | 1 | 600 |
|  | 2 | 1000 |
|  | 3 | 2800 |
|  | 4 | 1952 |
| None | 1 | 0 |
|  | 2 | 0 |
|  | 3 | 0 |
|  | 4 | 0 |

Excluding the multi-carboxylated starch, the most efficient thickening agents were the hydroxypropyl distarch phosphates. The carboxylated starch was more efficient only in the absence of cationic compounds. Cationic compounds, however, are incompatible with this starch as precipitation was observed with the monomeric conditioning agent after one day and was observed with the polymeric conditioning agents after two days. All other starches showed good compatibility with the cationic compounds. Further, the pre-gelatinization process influences the performance characteristics of the starch derivatives. Thus, the drum-dried hydroxypropylated distarch phosphate is much more efficient than the comparable non-crosslinked hydroxypropyl starch. Therefore, a particular derivatization is required for optimum efficiency. Surprisingly, the hydroxypropyl distarch phophate thickener efficiency was enhanced by the effect of the base. This makes the hydroxypropylated distarch phosphates particularly interesting for application in hair treatment products such as hair dying compositions and hair bleaching compositions. The viscosities of the pre-gelatinized starches and the cooking starches cannot directly be compared because the extent of starch swelling and shear degradation will be different.

In a further experiment, the influence of the pre-gelatinization process, of agglomeration, of cross-linking and of derivatization was investigated. The thickening efficiency of a series of pre-gelatinized starches was compared. The features of the tested starches and their thickening efficiency are reported in the table below.

| Starting Sstarch | Alkylation Type | Cross-linking | Pre-gelatini-zation | Ag-glomer-ation | Condi-tion | Viscosity, mPas, 45° C. |
|---|---|---|---|---|---|---|
| waxy maize starch | hydroxy-propyl | yes[1] | spray-dried[2] | yes | 1 | 4800 |
|  |  |  |  |  | 2 | 15563 |
| waxy maize starch | hydroxy-propyl | yes[1] | spray-dried[2] | no | 1 | 3738 |
|  |  |  |  |  | 2 | 13038 |
| waxy maize starch | hydroxy-propyl | yes[1] | drum-dried | no | 1 | 2738 |
|  |  |  |  |  | 2 | 6188 |
| waxy maize starch | none | no | spray-dried[2] | yes | 1 | 300 |
|  |  |  |  |  | 2 | 500 |
| waxy maize starch | acetyl | yes[1] | spray-dried[2] | yes | 1 | 3325 |
|  |  |  |  |  | 2 | 2563 |

[1]phosphorylated
[2]according to U.S. Pat. No. 4,280,851

The results show that the gelatinization process, cross-linking and alkylation had significant effects on thickening viscosity. Agglomeration appears to have a less significant effect on efficiency, although it does yield a performance advantage in terms of speed of dissolution. The spray dried pre-gelatinized, agglomerated, hydroxypropyl distarch phosphate was the most efficient starch derivative. The spray-dried, but not agglomerated, hydroxypropyl distarch phosphate was only slightly less efficient. A large decrease in thickening efficiency was associated with pre-gelatinization by drum-drying. Apparently, the extra shear involved in this pre-gelatinization process degrades the starch, reducing its thickening efficiency. The chemical modifications were also critical to the viscosity build up. Virtually no viscosity build was observed with the unmodified spray-dried starch. The acetylated pre-gelatinized starch was significantly less efficient than the hydroxypropylated pre-gelatinized starch. As a whole, the above experimental results show that the most efficient starch thickener is the spray-dried hydroxypropylated distarch phosphate made from waxy maize starch.

What is claimed:

1. A composition which comprises a continuous aqueous phase comprising a pregelatinized, crosslinked starch selected from the group consisting of a $C_2$–$C_5$ hydroxyalkyl starch and a $C_2$–$C_{18}$ acyl starch, which composition is for cleaning or caring for skin, teeth, or hair or for cleaning smooth surfaces.

2. The composition of claim 1, wherein the starch is at least one starch selected from the group consisting of a hydroxypropyl di-starch phosphate, a hydroxypropyl di-starch $C_4$–$C_{18}$ alkanoate, and a hydroxypropyl di-starch $C_1$–$C_{18}$ alkenoate.

3. The composition of claim 2, wherein the starch is a hydroxypropyl di-starch phosphate and has an amylopectin content of at least about 70%.

4. The composition of claim 3, wherein the starch is a spray-dried starch.

5. The composition of claim 4, wherein the spray-dried starch comprises largely intact starch granules.

6. The composition of claim 5, wherein the spray-dried starch granules are agglomerated to loose aggregates.

7. The composition of claim 4, wherein the spray-dried starch is (i) a uniformly pregelatinized, granular starch in the form of indented spheres in which least a majority of the starch granules are whole and unbroken and in the form of loosely connected agglomerates or individual granules; (ii) a non-granular starch which is substantially non-crystalline, non-retrograded, and completely predispersed; or (iii) a mixture thereof.

8. The composition of claim 3, wherein the aqueous phase is about 5 to about 98 wt. % and the aqueous phase comprises about 0.1 to about 20 wt. % of the starch.

9. The composition of claim 3, wherein the aqueous phase further comprises at least about 0.3 wt. % of at least one surfactant selected from the group consisting of non-ionic, anionic, cationic, and amphoteric surfactant.

10. The composition of claim 9, wherein the surfactant is about 7 to about 25 wt. %.

11. The composition of claim 9, wherein the composition has a pH of between about 2.5 and about 12.

12. The composition of claim 11, wherein the pH is about 4 to about 9.

13. The composition of claim 3, wherein the composition further comprises at least about 1 wt. % of a hydrophobic phase.

14. The composition of claim 13, wherein the hydrophobic phase is finely dispersed and is about 5 to about 25 wt. %.

15. The composition of claim 14, wherein the hydrophobic phase comprises at least one compound selected from the group consisting of a liquid or a solid fatty acid monoester, a fatty acid diester, a fatty acid triglyceride, a hydrocarbon, an alkyl ether, an alkyl ethoxylate, an alkyl propoxylate, an alkyl butoxylate, a silicone, and a long-chain alcohol.

16. The composition of claim 13, wherein the composition further comprises about 0.1 to 10 wt % of an emulsifier.

17. The composition of claim 16, wherein the emulsifier is at least one emulsifier selected from the group consisting of a partial ester of a polyhydric alcohol, an ethoxylate, a propoxylate, and a butoxylate.

18. The composition of claim 3, wherein the composition is a gel.

19. The composition of claim 18, wherein the composition further comprises about 5 to about 25 wt. % of a monohydric alcohol and/or polyhydric alcohol.

20. The composition of claim 19, wherein the monohydric alcohol is ethanol and the polyhydric alcohol is glycerin.

21. The composition of claim 3, wherein the composition is a hair dyeing composition which further comprises a colorant.

22. The composition of claim 3, wherein the composition is a hair bleaching composition which further comprises an oxidizing agent.

23. A composition which is a two part hair dyeing composition or a hair bleaching composition, with one part comprising a pregelatinized, crosslinked starch selected from the group consisting of a $C_2$–$C_5$ hydroxyalkyl starch, and a $C_2$–$C_{18}$ acyl starch and the other component comprising an aqueous phase.

24. The composition of claim 23, wherein the starch component is a powdered starch.

25. A cleaning composition selected from the group consisting of a shampoo, a hair conditioner, a shower gel, a bath foam, a liquid soap, and a dental cream, which comprises an aqueous phase which comprises a pregelatinized, crosslinked starch selected from the group consisting of a $C_2$–$C_5$ hydroxyalkyl starch and a $C_2$–$C_{18}$ acyl starch and at least about 0.3 wt. % of a nonionic, anionic, cationic, or amphoteric surfactant.

26. The composition of claim 3, which further comprises an additive selected from the group consisting of a preservative, a perfume, a flavor, a light protection agent, an antioxidant, a vitamin, a filler, a sequestrant, a coloring agent, a bronzing agent, a thickener other than the starch, an inorganic salt, a pH-regulator and a luster agent.

27. The composition of claim 21, which further comprises an additive selected from the group consisting of a preservative, a perfume, a flavor, a light protection agent, an antioxidant, a vitamin, a filler, a sequestrant, a coloring agent, a bronzing agent, a thickener other than the starch, an inorganic salt, a pH-regulator and a luster agent.

28. The composition of claim 25, which further comprises an additive selected from the group consisting of a preservative, a perfume, a flavor, a light protection agent, an antioxidant, a vitamin, a filler, a sequestrant, a coloring agent, a bronzing agent, a thickener other than the starch, an inorganic salt, a pH-regulator and a luster agent.

* * * * *